(12) United States Patent
Dickenson et al.

(10) Patent No.: US 12,043,915 B2
(45) Date of Patent: Jul. 23, 2024

(54) ELECTROPOLISHING OF MP35N WIRE FOR FATIGUE LIFE IMPROVEMENT OF AN IMPLANTABLE LEAD

(71) Applicant: Lake Region Manufacturing, Inc., Chaska, MN (US)

(72) Inventors: Roger C. Dickenson, Roanoke, VA (US); Wendy Hodges, Roanoke, VA (US); Jonathan Hardy, Roanoke, VA (US)

(73) Assignee: Lake Region Manufacturing, Inc., Chaska, MN (US)

( * ) Notice: Subject to any disclaimer, the term of this patent is extended or adjusted under 35 U.S.C. 154(b) by 873 days.

(21) Appl. No.: 17/062,746

(22) Filed: Oct. 5, 2020

(65) Prior Publication Data

US 2021/0102309 A1 Apr. 8, 2021

Related U.S. Application Data

(60) Provisional application No. 62/912,277, filed on Oct. 8, 2019.

(51) Int. Cl.
*C25F 3/16* (2006.01)
*A61N 1/04* (2006.01)

(52) U.S. Cl.
CPC ............... *C25F 3/16* (2013.01); *A61N 1/048* (2013.01); *A61N 1/0488* (2013.01)

(58) Field of Classification Search
None
See application file for complete search history.

(56) References Cited

U.S. PATENT DOCUMENTS

| 2,315,695 A | 4/1943 | Faust |
| 2,334,699 A | 11/1943 | Faust |
| (Continued) | | |

FOREIGN PATENT DOCUMENTS

| EP | 2416843 A1 | 2/2012 |
| JP | 2007006941 A | 1/2007 |
| WO | 2010117560 A1 | 10/2010 |

OTHER PUBLICATIONS

English translation JP 2007006941 (Year: 2007).*

(Continued)

*Primary Examiner* — Stefanie S Wittenberg
(74) *Attorney, Agent, or Firm* — Michael F. Scalise (57) ABSTRACT

MP35N (35% Co, 35% Ni, 20% Cr, 10% Mo, by weight) wires (solid and clad) are widely used for leads in cardiac rhythm management (CRM) and neurological electrical stimulation devices. Over the typical lifetime of a CRM device, a lead wire is subjected to stress cycling imposed by the heartbeat and is expected to survive 300 million stress cycles, or more. Premature fatigue fracture of a lead is sometimes caused by surface imperfections in the wire that has been coiled into the lead. The imperfections can result in concentration of stresses at a specific location on the wire surface. A vexing type of imperfection is a tiny surface fissure that is commonly referred to as a chevron. Wire drawing processes that are commonly used to form wires for manufacturing an implantable lead inherently produce a distribution of tiny chevrons on the wire surface. According to the present invention, removing chevrons and other surface imperfections using an electropolishing process helps reduce or eliminate premature fatigue failure initiated by such surface imperfection.

20 Claims, 5 Drawing Sheets

(56) References Cited

U.S. PATENT DOCUMENTS

| | | | |
|---|---|---|---|
| 2,338,321 A | 1/1944 | Faust | |
| 2,440,715 A | 5/1948 | Faust et al. | |
| 5,020,537 A | 6/1991 | Gunther | |
| 5,779,864 A | 7/1998 | Mikumo et al. | |
| 6,679,980 B1 | 1/2004 | Andreacchi | |
| 6,835,300 B2 | 12/2004 | Zhu et al. | |
| 7,169,286 B2 | 1/2007 | Qiao | |
| 7,252,746 B2 | 8/2007 | Schaeffer | |
| 7,357,854 B1 | 4/2008 | Andreacchi | |
| 7,627,382 B2 * | 12/2009 | Minar | A61N 1/056 607/115 |
| 7,776,189 B2 | 8/2010 | Shrivastava et al. | |
| 8,048,369 B2 | 11/2011 | Forbes Jones et al. | |
| 8,426,344 B2 | 4/2013 | Baecker et al. | |
| 8,588,933 B2 | 11/2013 | Floyd et al. | |
| 8,617,379 B2 | 12/2013 | Wong et al. | |
| 8,617,380 B2 | 12/2013 | Wong et al. | |
| 8,815,061 B2 | 8/2014 | Andreacchi et al. | |
| 8,916,226 B2 | 12/2014 | Mauch et al. | |
| 8,992,761 B2 | 3/2015 | Lin | |
| 9,173,733 B1 * | 11/2015 | Lim | A61F 2/958 |
| 9,320,623 B2 | 4/2016 | Ryan et al. | |
| 10,030,316 B2 | 7/2018 | Fujita et al. | |
| 2004/0117001 A1 | 6/2004 | Pelton et al. | |
| 2005/0090844 A1 | 4/2005 | Patel et al. | |
| 2005/0256563 A1 * | 11/2005 | Clerc | B23K 37/08 623/1.16 |
| 2005/0263171 A1 | 12/2005 | Wu et al. | |
| 2014/0014530 A1 * | 1/2014 | Lin | A61L 31/18 205/660 |
| 2014/0277392 A1 | 9/2014 | Webler, Jr. | |
| 2016/0243352 A1 * | 8/2016 | Raines | A61N 1/0556 |
| 2018/0291522 A1 | 10/2018 | Rokicki | |
| 2018/0303643 A1 | 10/2018 | Mitchell et al. | |

OTHER PUBLICATIONS

English translation CN 105568357 (Year: 2016).*
English translation WO 2013052528 (Year: 2013).*
Sullivan, et al., "The effects of surface processing on in-vivo corrosion of Nitinol stents in".
"European Search Report, Application No. 20200393.5 Dated Mar. 5, 2021".

* cited by examiner

ELECTROPOLISHING OF MP35N WIRE FOR FATIGUE LIFE IMPROVEMENT OF AN IMPLANTABLE LEAD

CROSS-REFERENCE TO RELATED APPLICATION

This application claims priority to U.S. provisional application Ser. No. 62/912,277, filed on Oct. 8, 2019.

BACKGROUND OF THE INVENTION

1. Field of the Invention

The present invention generally relates to wires made of MP35N® (35% Co, 35% Ni, 20% Cr, 10% Mo, by weight), which can be solid or have a core of a different electrically conductive metal clad with MP35N. More specifically, the present invention relates to electropolishing solid and clad MP35N wires. Following electropolishing, the thusly treated MP35N wire is formed into an implantable lead.

MP35N is a registered trademark of SPS Technologies, Inc., Jenkintown, Pennsylvania.

2. Prior Art

The use of MP35N in the manufacture of implantable leads in cardiac rhythm management and neurological electrical stimulation devices is well known. Over typical device lifetimes, a lead wire, regardless of its materials of construction, is subjected to stress cycling imposed by the heartbeat and is expected to survive 300 million stress cycles, or more. Premature fatigue fracture of an implanted lead is sometimes caused by imperfections in the wire from which the lead is constructed. The undesirable imperfections can result in concentration of stresses at a specific location on the wire surface. A vexing type of imperfection is a tiny surface fissure that is commonly referred to as a chevron.

The current state of wire forming is to draw a relatively large diameter wire through a series of progressively smaller dies to produce a wire of a final, lesser diameter. However, wire drawing processes inherently produce a distribution of tiny chevrons on the wire surface, so removing chevron imperfections helps reduce or eliminate premature fatigue failure of an implanted lead initiated by these features.

With relatively large diameter wires, mechanical methods such as shaving are commonly used to remove a surface layer from the wire. However, shaving is not feasible for wires, particularly wires of MP35N, that have the requisite relatively small diameters that are needed for making implantable medical leads, and the like. Implantable leads are typically made from wires having diameters that range from about 0.003 inches to about 0.008 inches.

Another commonly used technique for removing chevrons and similar types of imperfections from the outer surface of a wire is to remove a surface layer using a plasma or by sputtering. However, these methods are relatively slow and difficult to accomplish on long spools of wire.

Therefore, there is a need in the industry for a technique that is commercially viable for removing surface imperfections such as chevrons from the outer surface of a wire and that is applicable to the range of wire diameters that are typically used for implantable leads. Electropolishing MP35N wires (solid or clad) prior to forming them into implantable leads meets this need.

SUMMARY OF THE OF INVENTION

Implantable electrical leads used with pacemakers, defibrillators, and neurostimulators are subjected to fatigue stresses in service. Many implantable leads are made from a clad wire containing an alloy of MP35N jacketing a core of a different electrically conductive metal, for example, silver, gold, tantalum, platinum, and titanium. Prior to forming a lead, the MP35N wire had previously been drawn through a series of progressively smaller dies until a wire of a desired diameter is achieved. However, the wire drawing process is known to introduce tiny surface imperfections referred to as chevrons into the wire surface. A chevron and like imperfections can be the site of fatigue failure when the wire is coiled or braided or otherwise formed into an implantable lead. Therefore, a primary focus of the present invention is to improve the fatigue life of an implantable lead, particularly a lead comprising MP35N, by removing surface imperfections from the wire before it is coiled or braided into a lead.

According to the present invention, chevrons and other undesirable imperfections are substantially, if not completely, eliminated by electropolishing the MP35N wire to remove a thin layer from the outer surface of the wire. Electropolishing is a relatively rapid process that can be run fast enough to be commercially viable and is applicable to the range of wire diameters that are typically used for implantable leads. Electropolishing a wire that is intended to be manufactured into an implantable lead is performed continuously with the wire being fed from a first, payout spool, passing through the electropolish system including a tank containing an electropolishing solution, and then being wound up on a second, take-up spool. If desired, the equipment can be arranged to electropolish multiple spools of wire simultaneously.

In that respect, the present invention relates to an electropolishing operation that is performed after final wire drawing. This means that no upstream wire process changes are required. Regarding the degree or amount of surface removal, electropolishing is readily controllable using process parameters including, but not limited to, speed (time in the electropolishing solution), chemistry of the electropolishing solution, voltage/current of the power supply which establishes an electrical potential between the anodically-charge wire and cathode plates immersed in the electropolishing solution, and the temperature of the electropolishing solution. Additionally, the electropolishing process is relatively easy to monitor by measuring the final diameter of the wire using conventional equipment such as a laser micrometer. Furthermore, in addition to removing chevron imperfections, electropolishing produces a desirable smooth, bright surface finish.

The present invention further relates to taking the thusly electropolished wire, for example, an MP35N wire, and building it into a wound filar implantable medical lead. Over the typical lifetime of an implanted medical lead, the lead wires or filars are subjected to stress cycling imposed by the heartbeat, and the lead is expected to survive 300 million stress cycles, or more. Leads that are built from electrically conductive MP35N wires or filars that have been surface treated or electropolished according to the present invention are better suited to withstand this rigor without device failure than similar MP35N wires that have not been so treated.

These and other aspects of the present invention will become more apparent to those of ordinary skill in the art by reference to the following detailed description and the appended drawings.

DETAILED DESCRIPTION OF THE PREFERRED EMBODIMENTS

As used in herein, the term MP35N is defined according to ASTM F562 as a wrought 35% cobalt, 35% nickel, 20% chromium, 10% molybdenum, by weight, alloy for surgical implant applications.

Further, as used herein, when an MP35N wire is discussed, it is understood that the wire can be a solid MP35N wire or have a clad construction with an MP35N sheath or jacket cladding or covering a core of a different electrically conductive metal. Suitable core materials include silver, gold, tantalum, platinum, and titanium.

Figure 1:
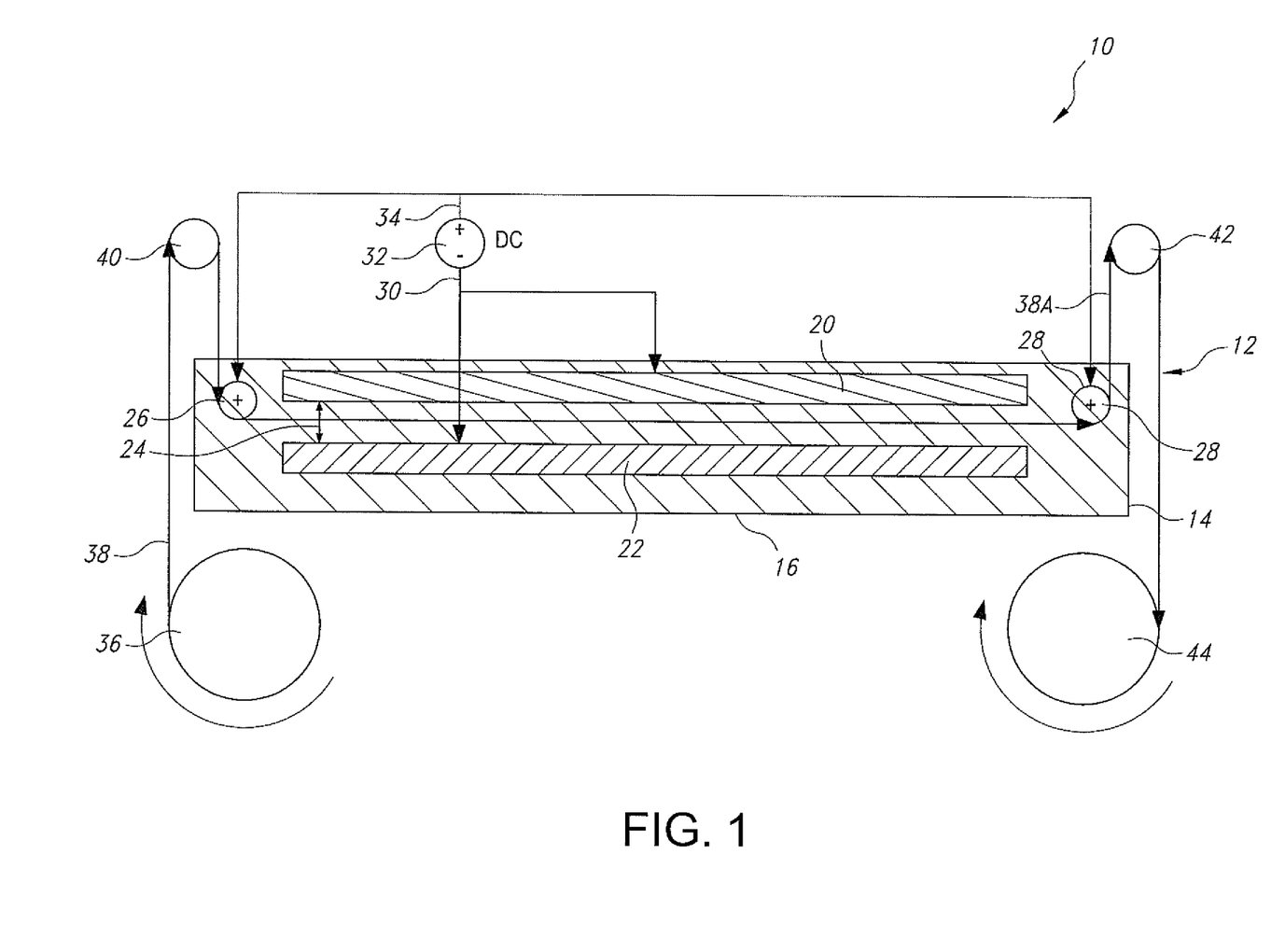
FIG. 1 is a schematic view of an electropolishing system 10 according to the present invention.

Turning now to the drawings, FIG. 1 is a schematic view of an electropolishing system or assembly 10 according to the present invention. The electropolishing system 10 has an open-ended tank or container 12 comprising a surrounding sidewall 14 supported on and extending upwardly from a bottom wall or base 16. An electropolishing solution 18 is contained in the tank 12. For cobalt-chromium alloys such as MP35N, suitable electropolishing solutions typically contain sulfuric acid mixed with water and/or a glycol compound. Suitable electropolishing solutions are described in U.S. Pat. No. 2,315,695 to Faust (from about 33% to about 50% sulfuric acid and from about 33% to about 40% glycerol, by weight, the balance being water). An exemplary solution is a mixture of about 15% to about 30% sulfuric acid in ethylene glycol. The temperature of the electropolishing solution 18 typically ranges from about 120° F. to about 175° F.

Other suitable electropolishing solutions are described in U.S. Pat. No. 2,334,699 to Faust (from about 5% to about 85% sulfuric acid and from about 5% to about 85% ortho phosphoric acid, the combined acid content being at least 50% but not over 90% by weight of the solution with the balance being water), U.S. Pat. No. 2,338,321 to Faust (from about 5% to about 80% sulfuric acid, from about 5% to about 80% phosphoric acid, and from about 0.5% to about 20% chromic acid, the combined acid concentration being above 50% but not over 90% by weight, the balance being water), U.S. Pat. No. 2,440,715 to Faust et al., U.S. Pat. No. 7,357,854 to Andreacchi, and U.S. Pat. No. 7,776,189 to Shrivastava et al., and U.S. Pub. No. 2014/0277392 to Webler, Jr.

A pair of upper and lower cathode plates 20 and 22 is positioned lengthwise in the tank 12, immersed in the electropolishing solution 18. A gap 24 resides between the cathode plates 20, 22. In an alternate embodiment, only one of the cathode plates is used. Anodically charged first and second or upstream and downstream brushes or pulleys 26 and 28 reside at opposed ends of the cathode plates 20, 22, also immersed in the electropolishing solution 18. Suitable materials for the cathode plates 20, 22 and the anode brushes or pulleys include materials that are resistant to degradation in the electropolishing solution 18 and that exhibit good conductivity, for example, titanium, zirconium, stainless steel, and copper.

The cathode side 30 of an electrical power supply 32 is electrically connected to the cathode plates 20, 22 immersed in the electropolishing solution 18. The anode side 34 of the electrical power supply 32 is electrically connected to the upstream and downstream anodically-charged pulleys 26, 28 immersed in the electropolishing solution 18. The power supply 32 typically delivers a direct current with voltages ranging from about 2 volts to about 30 volts. In an alternate embodiment, the electrical power supply 32 delivers an alternating current to the cathode plates 20, 22 and the upstream and downstream anodically-charged pulleys 26, 28.

A wire supply or payout spool 36 residing outside the electropolishing tank 12 carries a length of untreated wire 38 ranging in diameter from about 0.003 inches to about 0.008 inches that is intended to be treated in the electropolishing solution, for example, MP35N wire. In an electropolishing operation, untreated MP35N wire leaves the payout spool 36 and travels in a counterclockwise direction upwardly and over a first or upstream tensioning pulley 40 residing outside the electropolishing tank 12 where the wire 38 moves through an arc of about 180° to descend into the tank containing the electropolishing solution 18 and then to the upstream anodically-charged pulley 26. The upstream anodically-charged pulley 26 is positioned so that the unpolished wire 38 leaving the anode pulley 26 enters the gap 24 as an anodically-charge wire 38, aligned substantially parallel with the opposed major faces of the cathode plates 20, 22. An electrical potential of about 50 amps to about 600 amps per square foot of wire surface in the electropolishing solution 18 is applied between the anodically-charged wire 38 and the cathode plates 20 and 22, and this potential forces a surface layer ranging from about 0.00010 inches to about 0.00035 inches to dissolve from the wire 38 into the electropolishing solution. For example, with a wire having a diameter of 0.005" and with there being one foot of that wire in the electropolishing solution, there is 0.188 inch$^2$ or 0.0013 ft$^2$ of wire being polished. Accordingly, the appropriate current is from about 0.065 amps to about 0.785 amps.

The downstream anodically-charged pulley 28 is positioned so that after the wire 38 has travelled through the gap 24 between the cathode plates 20, 22, the thusly electropolished wire 38A contacts the downstream anodic pulley 28 to then travel through an arc of approximately 90° upwardly, out of the electropolishing solution 18 and to a downstream tensioning pulley 42. The electropolished wire 38A travels over the downstream tensioning pulley 42 through an arc of approximately 180° and onto a take-up spool 44. The take-up spool 44 is motor driven and controls the speed at which the untreated wire 38 is pulled from the payout spool 36 and through the electropolishing solution 18 in the tank 12.

While the payout and take-up spools 36, 44 are shown rotating in a counterclockwise direction, that is not required to practice the present invention. Depending on their positioning with respect to the electropolishing tank 12, the payout and take-up spools 36 and 44 can simultaneously rotate in a clockwise direction or one of them can rotate in a counterclockwise direction while the other rotates in a counterclockwise direction. What is important is that the take-up spool 44 is rotating at about the same speed as the payout spool 36. That way, the length of the untreated wire 38 leaving the payout spool 36 is substantially the same as the treated wire 38A being wound onto the take-up spool 44.

Moreover, the upstream and downstream tensioning pulleys 40 and 42 are configured to compensate for any change in relative speed with respect to the payout and take-up spools 36 and 44 so that the untreated wire 38 travels through the electropolishing solution 18 in the tank 12 at an even, regulated speed. Regulating the speed with which the wire 38 moves through the electropolishing solution 18 is important so that the thickness of material removed from the outer surface of the wire is held within a close tolerance. The goal is to only remove as much thickness as is necessary to significantly reduce, if not eliminate, all surface imperfections and fissures such as chevrons from the treated wire 38A without removing more material than is necessary.

As the treated or electropolished wire 38A passes out of the electropolishing solution 18 in the tank 12, its diameter is preferably monitored using a laser micrometer (not shown). If desired, an upstream laser micrometer (not shown) can be used to monitor the diameter of the untreated wire 38 entering the tank 12. That way, the thickness of material removed from the treated wire 38A is closely monitored and recorded. Thus, the amount of surface removal from the wire and its surface finish is controlled through various parameters including wire speed through the electropolishing solution 18, composition and temperature of the electropolishing solution, voltage and current from the electric power supply 32 delivered to the cathode plates 20, 22 and the anodically-charged pulleys 26, 28, cathode plate arrangement, and agitation of the electropolishing solution.

Figure 2:
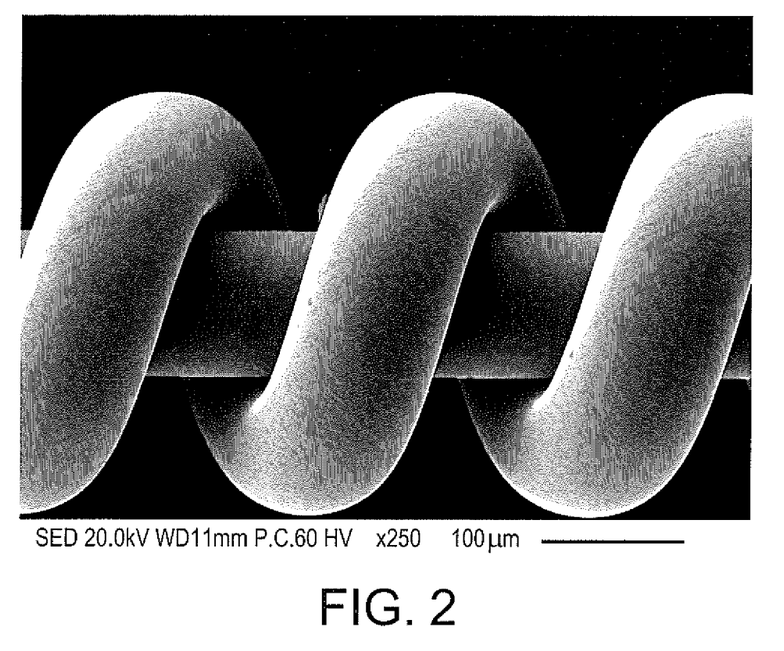
FIG. 2 is a photograph at ×250 magnification of an as-drawn MP35N coil.
Figure 2A:
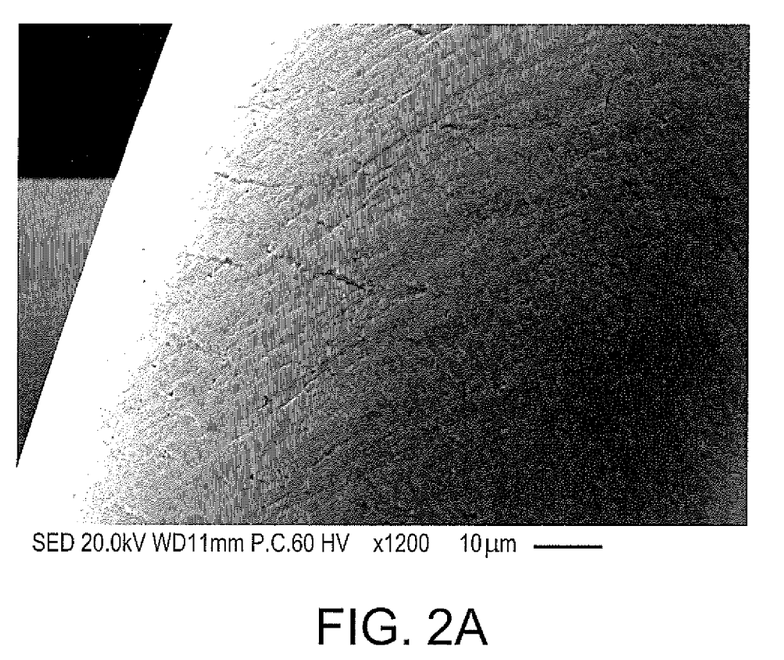
FIG. 2A is a photograph at ×1,200 magnification of the as-drawn MP35N coil shown in FIG. 2.
Figure 2B:
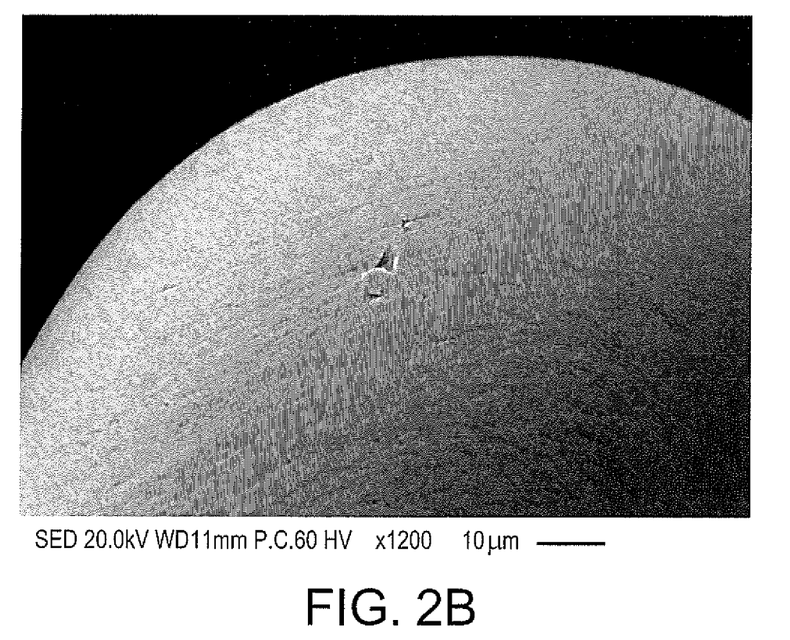
FIG. 2B is a photograph at ×1,200 magnification of the as-drawn MP35N coil shown in FIG. 2A, but from a different perspective.

FIGS. 2, 2A and 2B are photographs at ×250, ×1,200 and ×1,200 magnifications, respectively, of an MP35N wire that has been subjected to a progressive wire drawing process prior to being wound into a coil. Surface fissures are particularly apparent in FIGS. 2A and 2B as chevrons gouged into the outer surface of the wire by the drawing process.

Figure 3A:
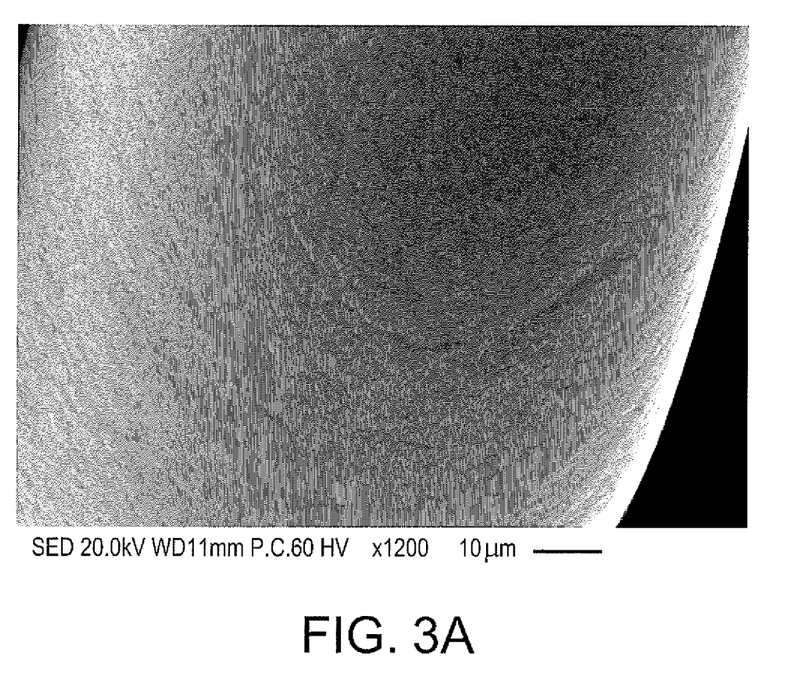
FIG. 3A is a photograph at ×1,200 magnification of a section of the electropolished MP35N wire cut from the as-drawn wire used to make the coils shown in FIGS. 2, 2A and 2B.
Figure 3B:
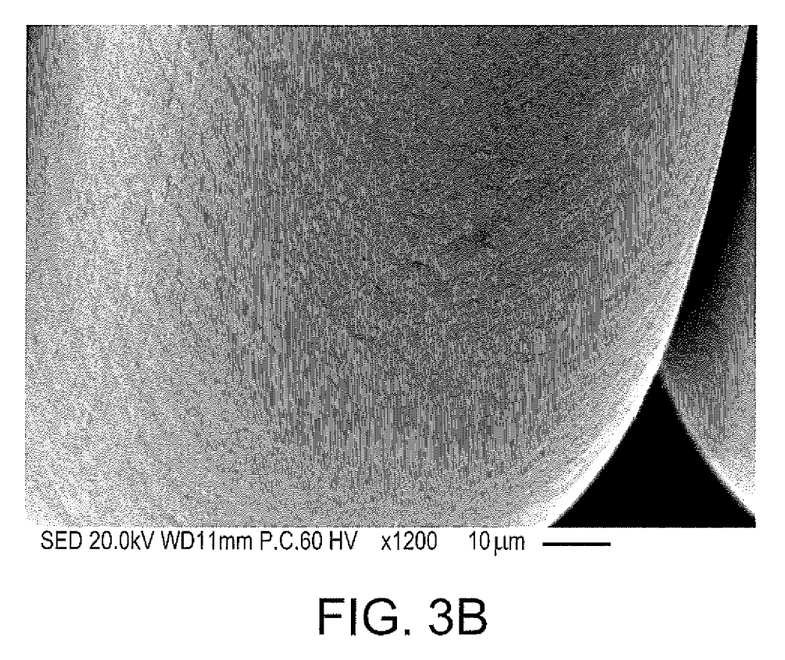
FIG. 3B is a photograph at ×1,200 magnification of a section of the electropolished MP35N wire cut from the as-drawn wire used to make the coils shown in FIGS. 2, 2A and 2B, but from a different perspective than the photograph of the wire shown in FIG. 3A.

In contrast, FIGS. 3A and 3B are photographs at ×1,200 magnification of a section of an electropolished MP35N wire cut from the as-drawn wire used to make the coils shown in FIGS. 2, 2A and 2B. It is apparent that the surface fissures shown in the photographs of FIGS. 2, 2A and 2B have been significantly reduced, if not eliminated.

Supplementary operations may be applied to the wire before and after electropolishing. For example, it may be advantageous for the untreated wire 38 to be cleaned in a commercial alkaline detergent before electropolishing and rinsed and dried after electropolishing. Such supplementary operations are performed in-line with the electropolishing operation.

In the art of lead manufacturing, an electrical conductor, for example, the electropolished MP35N wire 38A, is often referred to as a "filar".

The electropolished wire 38A is now acceptable for incorporation into an implantable medical lead 50 (FIG. 4) according to the present invention. That is, the electropolished wire 38A that has had an outer surface layer ranging from about 0.00010 inches to about 0.00035 inches removed from the untreated wire through treatment in the electropolishing system 10 shown in FIG. 1 so that surface fissures such as chevrons, and the like, have been significantly reduced, if not eliminated, is manufactured into an implantable lead. An implantable lead 50 is expected to survive 300 million stress cycles, or more. Leads that are built from electrically conductive MP35N wires or filars 38A that have been surface treated according to the present invention are believed to be better suited to withstand the rigors of millions of stress cycles without device failure than similar MP35N wires that have not been treated. That is because lead failure due to chevron-type surface fissures, and the like, have been greatly reduced, if not eliminated.

Figure 4:
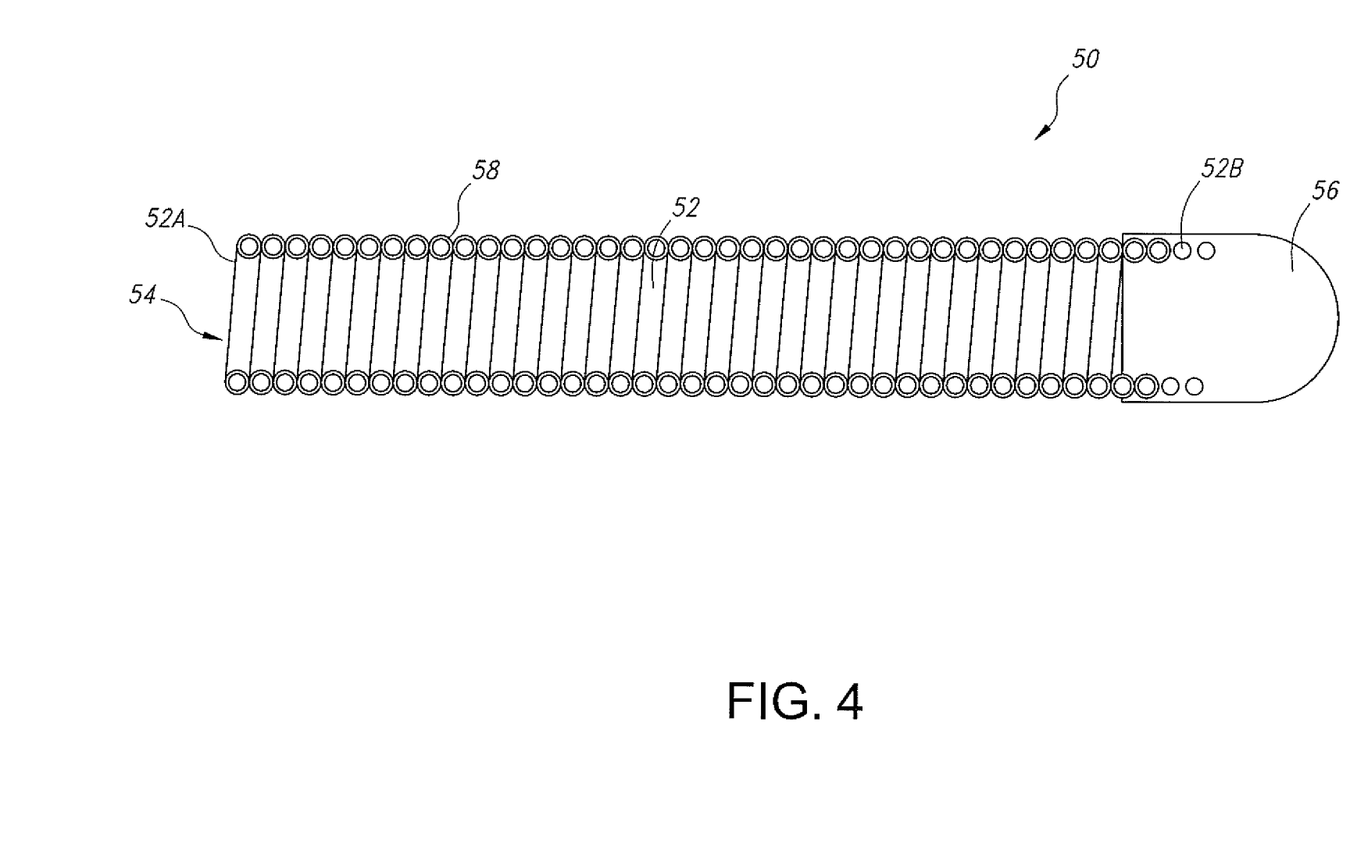
FIG. 4 is a perspective view of an exemplary lead 50 formed from an electropolished wire 38A that had previously been subjected to the electropolishing system 10 shown in FIG. 1.

FIG. 4 illustrates that one, two, three, four or more of the electropolished wires or filars 38A have been interwound into an exemplary elongate and flexible cylindrically-shaped coil 52 extending to a proximal end 52A and a distal end 52B. In the illustrated embodiment, the coil 52 defines a lumen 54. While not shown in the drawing, the proximal end 52A of the coil is configured for secure connection to an electrical contact or connector that is connectable to an implantable medical device such as a cardiac pacemaker, cardiac defibrillator, neurostimulator, and the like. A pacing/sensing electrode 56 that is configured for physical contact with body tissue, for example, myocardial tissue is electrically secured to the distal end 52B of the multi-filar coil 52.

Preferably, the filars comprising the multifilar coiled lead 50 are provided with an insulative coating 58. A suitable insulative coating 58 is an insulative polyimide or fluoroimide coating. A suitable insulative polyimide coating is described in U.S. Pat. No. 7,627,382 to Minar et al., titled "Medical Devices with Aromatic Polyimide Coatings," the disclosure of which is incorporated herein by reference. The insulative coating 58 has a thickness of about 0.001 inches and helps prevent electrical "shorts" between side-by-side filars in a multifilar lead construction where one of the filars is electrically connected to a first electrode and a second filar is electrically connected to a second electrode. The insulative coating also helps prevent electrical conductivity to other conductive pathways within the body.

One skilled in this art will recognize that the number of filars 38A and their coupling to the pacing/sensing electrode 56 has many possible coil and electrode/contact combinations. Moreover, different combinations of the number of filars coupled to an electrode can be used. For example, in a quadrifilar construction, two filars could be coupled to one electrode or contact and two filars could be coupled to a second electrode or contact. Alternatively, three of the four filars could be coupled to a first electrode or contact and the fourth filar coupled to a second electrode or contact.

Thus, the present invention relates to improvements in the construction of implantable medical leads. MP35N, which is a material that is well known for use in building medical leads, is often subjected to a progressive die drawing process to obtain a desired wire diameter prior to lead manufacture. However, it is known that drawing a wire through a series of progressively smaller dies is prone to introduce surface fissures such as chevrons into the wire surface. These surface imperfections can be the situs or place of fatigue failure, especially as a lead is subjected to over 300 million stress cycles during its useful life in a cardiac pacing application. A novel method for removing surface imperfections before the wire is coiled into a lead is to move the wire through an electropolishing bath to remove a thin surface layer containing the surface imperfections and fissures to thereby provide the thusly treated wire. According to the present invention, electropolishing a wire, particularly a MP35N wire (solid or clad), is an advancement in the art as it is believed to result in a coiled lead that is better capable of being subject to millions of stress cycles without failing than a similar wire that has not been electropolished.

It is appreciated that various modifications to the present inventive concepts described herein may be apparent to those of ordinary skill in the art without departing from the scope of the present invention as defined by the herein appended claims.

What is claimed is:

1. A method for manufacturing an implantable medical lead, comprising the steps of:
   a) providing a length of MP35N wire having a first diameter, wherein the length of MP35N wire has a distribution of chevrons in a surface layer ranging from about 0.00010 inches to about 0.00035 inches, and wherein the MP35N wire has 35% Co, 35% Ni, 20% Cr, 10% Mo, by weight;
   b) electropolishing the MP35N wire to remove the surface layer ranging from about 0.00010 inches to about 0.00035 inches from the length of wire to thereby provide a treated length of MP35N wire having a second diameter that is less than the first diameter, wherein the treated length of MP35N wire having the second diameter is substantially devoid of any chevrons; and
   c) after the treated length of MP35N wire having the second diameter is provided, winding at least a portion of the treated length of MP35N wire into an implantable medical lead so that all of the treated length of MP35N wire comprising the implantable medical lead has the second diameter.

2. The method of claim 1, including providing the length of MP35N wire being a solid MP35N wire.

3. The method of claim 1, including providing the length of MP35N wire comprising MP35N cladding an electrically conductive metal core.

4. The method of claim 3, including selecting the electrically conductive metal core from silver, gold, tantalum, platinum, and titanium.

5. A method for manufacturing an implantable medical lead, comprising the steps of:
   a) providing a length of MP35N wire having a first diameter, wherein the length of MP35N wire has a distribution of chevrons in a surface layer ranging from about 0.00010 inches to about 0.00035 inches, and wherein the MP35N wire has 35% Co, 35% Ni, 20% Cr, 10% Mo, by weight;
   b) providing a tank containing an electropolishing solution;
   c) providing an electrical power supply, wherein a cathodic side of the electrical power supply is electrically connected to at least one cathode plate immersed in the electropolishing solution and an anodic side of the electrical power supply is electrically connected to upstream and downstream anodically-charged contacts immersed in the electropolishing solution, the upstream and downstream anodically-charged contacts being positioned upstream and downstream with respect to the at least one cathode;
   d) moving the MP35N wire into the electropolishing solution with the MP35N wire being in contact with the upstream and downstream anodically-charged contacts and in close proximity to the at least one cathode so that an electrical potential between the MP35N wire and the cathode removes the surface layer ranging from about 0.00010 inches to about 0.00035 inches from the length of MP35N wire to thereby provide a treated length of MP35N wire having a second diameter that is less than the first diameter, wherein the treated length of MP35N wire having the second diameter is substantially devoid of any chevrons;
   e) after the treated length of MP35N wire having the second diameter is provided, winding at least a portion of the treated length of MP35N wire into a coil having a coil proximal end and a coil distal end so that all of the treated length of MP35n wire comprising the coil has the second diameter; and
   f) attaching a proximal electrical connector to the coil proximal end and attaching an electrode that is configured to contact body tissue to the coil distal end to thereby provide an implantable medical lead.

6. The method of claim 5, including providing the length of MP35N wire being a solid MP35N wire.

7. The method of claim 5, including providing the length of MP35N wire comprising MP35N cladding an electrically conductive metal core.

8. The method of claim 7, including selecting the electrically conductive metal core from silver, gold, tantalum, platinum, and titanium.

9. The method of claim 5, including providing the length of MP35N wire having the first diameter ranging from about 0.003 inches to about 0.008 inches.

10. The method of claim 5, including providing the electrical potential between the MP35N wire and the cathode having a current density ranging from about 50 amps to about 600 amps per square foot of the MP35N wire in the electropolishing solution.

11. The method of claim 5, including providing the electropolishing solution comprising sulfuric acid mixed with at least one of water and ethylene glycol.

12. The method of claim 5, including providing the electropolishing solution comprising a mixture of 15% to 30% sulfuric acid in ethylene glycol.

13. The method of claim 5, including winding from one to four treated MP35N wires having the second diameter into the coil comprising the implantable medical lead.

14. The method of claim 5, including coating at least a portion of the treated length of MP35N wire having the second diameter with an insulative polyimide or fluroimide coating prior to winding at least the portion of the treated length of MP35N wire into the coil comprising the implantable medical lead.

15. The method of claim 14, including providing the insulative coating having a thickness of about 0.001 inches.

16. The method of claim 5, including providing the coil defining a lumen.

17. The method of claim 5, including providing the proximal electrical connector being configured for electrically connecting the medical lead to an electronic device.

18. The method of claim 5, including providing the electrode being configured for at least one of stimulation and sensing of body tissue.

19. The method of claim 5, including subjecting an MP35N wire to a progressive die drawing process to thereby provide the length of MP35N wire having the first diameter.

20. A method for manufacturing an implantable medical coil, comprising the steps of:
   a) providing a length of MP35N wire having a first diameter, wherein the length of MP35N wire has a distribution of chevrons in a surface layer ranging from about 0.00010 inches to about 0.00035 inches, and wherein the MP35N wire has 35% Co, 35% Ni 20% Cr, 10% Mo, by weight;
   b) electropolishing the MP35N wire to remove a surface layer ranging from about 0.00010 inches to about 0.00035 inches from the length of wire to thereby provide a treated length of MP35N wire having a second diameter that is less than the first diameter, wherein the treated length of MP35N wire having the second diameter is substantially devoid of any chevrons; and c) after the treated length of MP35N wire having the second diameter is provided, winding at least a portion of the treated length of MP35N wire into a coil so that all of the treated length of MP35N wire comprising the coil has the second diameter.

\* \* \* \* \*